United States Patent
Maletz et al.

(10) Patent No.: US 8,008,367 B2
(45) Date of Patent: Aug. 30, 2011

(54) COMPOSITE MATERIAL AND USE OF A COMPOSITE MATERIAL

(75) Inventors: Reinhard Maletz, Cuxhaven (DE); Stefan Kruschel, Cuxhaven (DE); Manfred Thomas Plaumann, Cuxhaven (DE)

(73) Assignee: VOCO GmbH, Cuxhaven (DE)

( * ) Notice: Subject to any disclaimer, the term of this patent is extended or adjusted under 35 U.S.C. 154(b) by 356 days.

(21) Appl. No.: 10/534,176

(22) PCT Filed: May 22, 2003

(86) PCT No.: PCT/EP03/05338
§ 371 (c)(1),
(2), (4) Date: May 5, 2005

(87) PCT Pub. No.: WO2004/043409
PCT Pub. Date: May 27, 2004

(65) Prior Publication Data
US 2006/0116438 A1 Jun. 1, 2006

(30) Foreign Application Priority Data

Nov. 13, 2002 (DE) .................. 102 53 481

(51) Int. Cl.
*A61K 6/08* (2006.01)
*A61K 6/02* (2006.01)
*A61C 5/00* (2006.01)

(52) U.S. Cl. ........ 523/116; 523/105; 523/113; 523/117; 433/226

(58) Field of Classification Search .................. 523/115, 523/116, 105, 113, 117; 433/228.1, 226
See application file for complete search history.

(56) References Cited

U.S. PATENT DOCUMENTS

| | | | |
|---|---|---|---|
| 4,215,033 A | 7/1980 | Bowen | 260/42.15 |
| 4,217,264 A | 8/1980 | Mabie et al. | 260/42.15 |
| 4,839,215 A | 6/1989 | Starling et al. | 428/131 |
| 5,852,096 A * | 12/1998 | Heindl et al. | 524/492 |
| 5,936,006 A * | 8/1999 | Rheinberger et al. | 523/116 |
| 6,362,251 B1* | 3/2002 | Alkemper et al. | 523/116 |
| 2002/0022677 A1* | 2/2002 | Teramae et al. | 523/113 |
| 2002/0045149 A1* | 4/2002 | Alkemper et al. | 433/212.1 |
| 2002/0193463 A1* | 12/2002 | Jones et al. | 523/115 |
| 2005/0256222 A1* | 11/2005 | Jones et al. | 523/116 |

FOREIGN PATENT DOCUMENTS

| | | |
|---|---|---|
| DE | 24 03 211 | 7/1975 |
| DE | 24 05 578 | 8/1975 |
| DE | 34 03 040 | 8/1985 |
| DE | 196 15 763 | 10/1997 |
| DE | 198 45 556 | 4/2000 |
| EP | 0 004 868 | 10/1979 |
| EP | 0 172 513 | 2/1986 |
| EP | 0 382 033 | 8/1990 |

OTHER PUBLICATIONS

Abstract of WO 00 25729, Published May 11, 2000, for "Improved Filler for Dental Composite Materials".
Abstract of WO 96 26237, Published Aug. 29, 1996, for "Improved Composite Material".

* cited by examiner

*Primary Examiner* — Mark Eashoo
*Assistant Examiner* — Michael Pepitone
(74) *Attorney, Agent, or Firm* — Vidas, Arrett & Steinkraus P.A.

(57) ABSTRACT

Composite material with a polymerisable organic binder, characterised in that it contains a filler with filler particles which have the shape of a torus.

15 Claims, 3 Drawing Sheets

COMPOSITE MATERIAL AND USE OF A COMPOSITE MATERIAL

CROSS-REFERENCE TO RELATED APPLICATIONS

Not Applicable

STATEMENT REGARDING FEDERALLY SPONSORED RESEARCH

Not Applicable

The present invention relates to a composite material with a specific filler and the use of a composite material with a specific filler for dental purposes.

BACKGROUND OF THE INVENTION

Composite materials are composites made from a plastics material and inorganic filling materials. Conventionally, therefore, they consist primarily of three different components: a polymerisable organic matrix, filler particles and an agent which ensures the bond between the polymer and the filler particles. Dental restorative materials represent a specific form of composite materials as they are subjected to the greatest demands, due to the extreme physical and chemical stress in the extremely inhospitable environment of the mouth. Due to their extensive requirement profile, these materials often serve as a basis for developing non-dental composites or as a model for use in the non-dental field.

Dental restorative composite materials have been used for over 40 years for fillings, linings and fixings, as stump restoration, crown and bridge, prosthesis and relining material, as filled adhesives which produce adhesion on dental enamel, plastics, ceramics or metal, and as dental sealing compositions. After being introduced into the cavity, composites cure in a polymerisation reaction, either chemically or by the addition of external energy.

The organic polymerisable component of the dental composite material is generally cross-linked in a radical reaction and contains corresponding ethylenically unsaturated functional groups. The monomers and oligomers comprise mono-, di- and/or polyacrylates and/or methacrylates, such as for example diglycidylmethacrylate of bisphenol A ('Bis-GMA', 2,2-bis[4(2-hydroxy-3-methacryloxypropyloxy)-phenyl]propane) and diurethane di(meth)acrylate from 2,2,4-Trimethylhexamethylenediisocyanate and 2-hydroxyethyl (meth)acrylate (UDMA). When referring to methacrylates, analogous acrylates are also understood. Commercially obtainable standard mixtures contain Bis-GMA, UDMA and triethyleneglycoldimethacrylate to reduce the viscosity.

In order to be able to carry out radical curing of the resin composition, an initiator system is added to the mass which triggers the radical polymerisation following radiation and/or a redox reaction process. A typical system which initiates the radical polymerisation of the methacrylate consists of a photoinitiator (ketone) and an accelerator (amine). Typically, camphorquinone is used as a ketone and para N,N-Dimethylaminobenzoic acid as an amine. Further photoactive components can be admixed to the mixture. If the composition is exposed to light with a suitable radiation source at 460 nm, the composite material is photochemically cross-linked. Alternatively, the material can also be chemically cross-linked. To this end, the peroxide/tertiary amine combination is used as a redox system. The two components have to be kept separated from one another in a 2-component system. After mixing the two components free radicals are generated and the radical polymerisation of the acrylates cures the composite material. As no external aids are required with this type of curing, this system is also known as self-curing.

Composite compositions can therefore be designed as either self-curing or photochemically curing (mono-cure). Furthermore, composite compositions can be formulated which represent a combination of self-curing and photochemically curing systems (dual-cure). If polyacrylic acid or a derivative of polyacrylic acid is added to one part of the 'dual-cure' composite system and basic glass is present in the other part, under suitable conditions, this system also cures in an acid base reaction (triple-cure) in addition to a chemical and photochemical mechanism.

The inorganic filling materials of the dental composite material generally consist of quartz, borosilicate glass, lithium aluminium silicate, barium aluminium silicate, strontium/barium glass, zinc glass, zirconium silicate, pyrogenic or colloidal silicic acid.

The bond of the inorganic filling materials with the organic resin matrix is generally ensured by the use of coupling agents or adhesion promoters. This is essential for the subsequent suitability of the composite mass as a dental material. In this connection, the filler, generally in the presence of weak acids, is treated with a silane before it is mixed with the liquid resin component. The method for preparing silanized filler surfaces consists in firstly adjusting an ethanol/water mixture (generally 95/5% by volume) with acetic acid to a pH value of 4.5-5.5. The silane is then added in such an amount that a solution strength of ca. 2% results. Within 5 minutes the alkoxysilyl groups are hydrolysed and the siloxane formation commences. Then the filler to be processed is added to the solution by continuous mixing. Within a few minutes the silane is adsorbed by the filler and the surface of the filling material loaded with adhesion promotor. The solution is decanted off and the particles washed twice with ethanol. Finally, the remaining silanol functions are condensed for a few minutes at 110 DEG C and 24 hours at room temperature.

The silane acts as a surface active material which compatabilises the surface of the filler with the resin matrix and ensures a rigid bond between the organic and inorganic material. Amongst others, 3-methacryloyloxypropyltrimethoxysilane has proved to be a particularly suitable silane for creating a bond between the inorganic and organic phase. A portion of the hydrolysed alkoxysilyl groups of the silane reacts directly with the hydroxyl groups on the mineral surface of the filler, while the other portion fuses together and thus produces a continuous layer of the coupling agent on the filler surface. During the course of the subsequent radical polymerisation of the dental composite mass, the methacryloyloxypropyl functions of the silane layer continuously adhering to the filler surface are then polymerised in the organic resin phase and thus form a permanent bond between the hydrophilic fillers and the hydrophobic resin matrix.

The properties of the resulting dental composite material is determined primarily by the inorganic phase. Whilst Young's modulus (E-module) for an unfilled resin system based on Bis-GMA is 2.8 GPa, the dental enamel has a value of 83 GPa and the dentine a value of 19 GPa. By adding a conventional silylated filler to the Bis-GMA-resin the value of 2.8 GPa can be markedly improved. If the filler is added to the resin in the volume ratio of 1 to 1.25, Young's modulus can be raised to a value of 10 GPa. For a ratio of 1:1 a value of 15 GPa can be achieved.

The type of filler, the amount and distribution of particles for a given resin composition determine the mechanical, aesthetic and rheological characteristics of the dental composite moulded material, such as surface hardness, abrasion resistance, wear resistance, pressure resistance, tensile strength, polymerisation shrinkage, fracture resistance and thermal shock resistance as well as polishability, shine, opacity, translucence and colour stability, as well as flow characteristics, stability and modelability. As a rule of thumb, the higher the concentration of silanized filler in the liquid resin, the better the mechanical, physical and chemical properties of the cured moulded material.

Against the background of the paramount importance of the inorganic phase for the properties of dental composite materials, the traditional division of dental composite materials is understood to be into three different basic groups.

A macrofilled composite material is a highly filled composition (up to 87 wt. %) with relatively large particles (1-100 μm). Whilst previously, glass powder with average particle sizes of 30-50 μm served as the filler, nowadays the filler is generally ground quartz or even glass ceramics with an average particle size of 8-12 μm. Macrofilled composites have the best wear resistance, but due to the particle size high polishing is extremely difficult. During polishing the bulky filler particles break out of the filling, small holes remain behind and the broken-out filler fragments exert an abrasive effect on the remaining moulded material, so that macrofilled composites cannot be highly polished and have a fundamental aesthetic flaw.

In order to comply with the demand for improved aesthetics, the group of microfilled dental composite materials was developed. A characteristic feature of these groups is the exceptionally small particle size of the composite filler which primarily consists of amorphous silicic acid and has an average particle size of ca. 0.04 μm. This small particle size results in an extremely large particle surface which, due to intensive interaction forces between the particle surfaces, in turn sets a premature limit for the filler concentration of the composite material. As a rule, microfilled composite materials cannot be mixed with filler of more than 50 wt. %, as the material is then no longer workable due to higher viscosity. This composite group may be highly polished, exhibits excellent refractive properties and fulfils all criteria of an exceptionally aesthetically effective dental material. As a result of the low filler content, microfilled materials, compared to macrofilled dental composites, however, exhibit considerably reduced mechanical properties such as abrasion, tensile strength, excessive shrinkage, etc.

It has been attempted on many occasions, but until now without success, to increase the filler content, for example by the incorporation of pyrogenic silicic acid into prepolymerised resin particles (25 μm), agglomerated or sintered particles and thus to increase the strength.

By attempting to combine the polishability of the microfilled composites with the excellent mechanical properties of the macrofilled composites, the group of so-called hybrid composites was developed. In this connection, the filler used is a mixture of conventional glass with a particle size of 0.6-1.5 μm and of nanoscale particles of 0.01-0.05 μm. As a rule, the quantifiable portion of nanoscale silicic acid particles is 7-15 wt. %. The entire filler content can be up to 80 wt. %. Due to large variations in the particle sizes, an exceptionally compact packing density of the filler particles can be achieved, smaller particles being located in the spaces between the larger particles.

An example for the composition of a microfilled system is disclosed in DE 2403211. Hybrid materials are known from the patents DE 2405578, DE 3403040 and EP 382033.

BACKGROUND OF THE INVENTION

Although, due to improvements in materials science, modern composite fillers are a permanent fixture in the treatments available to dentists, even in the side tooth area, these systems nevertheless have several fundamental drawbacks which are primarily linked with the 'bond' between the organic resin matrix and the inorganic filler surfaces. The silane coupling agents form 'siloxane bonds' with minerals. These bonds which ensure the bond between the two phases, may be hydrolysed, like any bond between an organic polymer and a hydrophilic, mineral material surface. Hydrolysis of the siloxane bond however produces hydrolytic degradation in the polymer, increased crack formation along the material/resin interfacial region, water absorption, softening effects in the polymer, swelling of the composite, reduced wear resistance, abrasion resistance and colour stability, due to the filler breaking out. Finally, the bond of the two phases is broken.

The advantage of silane relative to other adhesion promoters lies in its characteristic of behaving in a reversible manner with regard to hydrolytic bond cleavage. The thermodynamic equilibrium lies broadly on the side of the siloxane bond formation. Although the equilibrium amount of water molecules is therefore more important on the polymer/solid interface layer than the diffusion rate of the water in the polymer, water entering the material will however set the hydrolytic degradation process in motion. In the presence of strongly hydrophobic resins, water itself reaches the polymer/solid interface by diffusion. Once the interface layer is attacked, the water is attached there in the form of clusters, the bond of the organic phase to the inorganic phase is loosened and the structure of the composite broken up by osmotic pressure.

To improve the bond between filler and polymer matrix, the possibility was considered to create a physical adhesion in addition to the chemical adhesion. In U.S. Pat. No. 4,215,033 a semi-porous filler is produced by etching glass. Microporous fillers for use as dental materials are known from the publications U.S. Pat. No. 4,217,264, EP 4868, EP 172513, DE 19846556 and DE 19615763. With the physical adhesion, resin penetrates into the pores of the filler and thus after polymerisation anchors the organic with the inorganic phase, as the cured resin is held tightly in the pores of the filler. Thus an improved structural integrity of the moulded material is ensured.

The principle of the physical anchoring of filler and matrix which is disclosed in DE 19615763 and includes the use of porous $SiO_2$ particles, has however three principal disadvantages. The first consists of the extremely expensive production of the porous filling materials which includes a very expensive phase separation step, and grinding and screening processes. The second disadvantage lies in the very small pore diameter which is preferably 90-100 nanometers. In order to ensure an effective inflow of the resin into the pores, resin composites of very low viscosity must be used with low surface tension. This is obtained by the use of dimethacrylates with a low molecular weight, such as for example triethyleneglycoldimethacrylate (TEDMA) or hexanedioldimethacrylate (HDDMA). A higher proportion of these low molecular monomers leads however to increased composite shrinkage. Alternatively, the viscosity of the matrix can also be reduced by the addition of monomethacrylates, such as for example hydroxypropylmethacrylate (HPMA) or triethyleneglycolmonoethylethermonomethacrylate. The use of monomethacrylates leads to a poorer cross-linking of the polymer, compared to dimethacrylates and thus to lower flexural strength and greater discolouration. The third disadvantage lies in the restriction of the production process to silicon dioxide fillers which do not allow a clinically acceptable radiopacity to be set.

In spite of enormous improvements in the field of dental composite materials, the problem of the phase bond however remains unsolved, as even with the use of porous fillers, it can lead to the release of the polymer matrix from the inorganic filler by means of hydrolytic cleavage. It is therefore the object of the invention to provide a filler which forms a stable bond with the organic phase and allows such a strong physical bond between it and the binder of the dental material that possible hydrolysis can no longer destroy the bond once it is formed, and a composite material containing this filler which, due to the stable bond between the phases, ensures improved properties relative to the prior art.

DETAILED DESCRIPTION OF THE INVENTION

Figure 1:
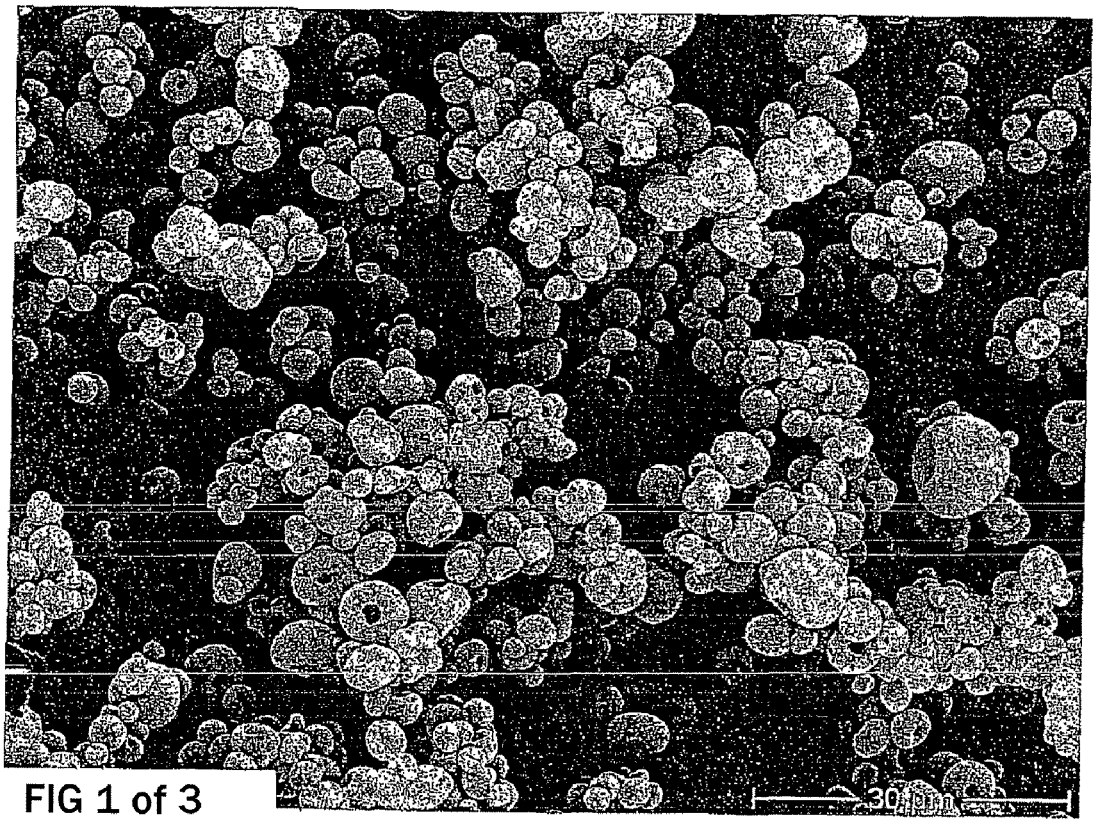
FIG. 1 is a SEM picture of $SiO_2$ particles with a torus structure.

While this invention may be embodied in many different forms, there are described in detail herein a specific preferred embodiment of the invention. This description is an exemplification of the principles of the invention and is not intended to limit the invention to the particular embodiment illustrated The invention relates to a specific filler with filler particles which comprise a spherical annular structure and structurally correspond to the geometry of a torus. In contrast to porous fillers, in which the resin is merely mechanically anchored in the pores of the filler particles, here the extreme case is realised where the filler is completely drawn through by a single pore. This leads to the organic phase being continually bonded with the inorganic phase and thus forms a particularly effective linkage from a mechanical point of view. In this connection, the torus-shaped filler particles are mechanically penetrated by binders, like a string of beads, and bonded to one another by the continuous resin phase present in the interior of the torus, such that they can no longer be released from the resin matrix by hydrolytic degradation. Thus a dental material is produced which, due to the extremely effective bond between the organic and inorganic composite phase, has a particularly pronounced abrasion resistance with high flexural strength at the same time, which cannot be achieved by comparable dental materials of the prior art. As the hydrolytic degradation which starts over a period of time, also no longer leads to a phase separation because of the solid phase bond, the durability of the dental material is extended with full functionality. At the same time the aesthetic character of the dental mass is also increased. During polishing the filler particles, due to the solid phase bond with the binder, are worn away in layers and not, as with macrofilled composites, broken as a whole from the polymer matrix. This allows a high polish.

Suitable binders for composite materials are, in addition to ethylenically unsaturated monomers and oligomers, epoxides, ormocers, ceramers, liquid crystal systems, spiro-orthoesters, oxethanes, polyurethane, polyester, A-silicon and C-silicon, polycarboxylic acids, etc.

Further possible components of the composite material include colorants, pigments, stabilisers, co-initiators, wetting agents, radiopacifiers, etc.

Moreover, the invention further relates to composite materials which include the filler with torus-shaped filler particles for non-dental purposes and to the filler with torus-shaped filler particles for any purposes.

A further aspect of the invention relates to the following disclosed method for producing the torus-shaped filler particles.

The annular, spherical fillers can be created from amorphous, nanoscale $SiO_2$ primary particles. To this end, colloidal silica gels are preferably used as suspension in water (silica sols). These silica gels can contain both ammonium, aluminium and sodium as stabilising counterion. The preferred primary particle size is approx. 5-100 nm, the generally preferred primary particle size being 10-50 nm. Common $SiO_2$ suspensions are, for example, Ludox AS40 or Ludox HS40 (Aldrich Chemical Company, Milwaukee, USA).

In order to provide sufficient radio-opacity of the dental material, heavy metal oxides in combination with $SiO_2$ are incorporated in the annular fillers. Preferably the heavy metal oxides are used with an atomic number of greater than 28. Oxides of yttrium, strontium, barium, zirconium, tungsten, tin, zinc, lanthanum or ytterbium or combinations thereof are particularly preferably used. The heavy metals can be incorporated in the production process in the form of solutions, sols or particle suspensions. In this connection, the preferred size of the heavy metal particle is 5-100 nm, the particularly preferred size, 10-50 nm. As precursors for the heavy metal oxides, water soluble inorganic or organic salts of the corresponding metals, such as for example salts of aliphatic mono or dicarboxylic acids or even alkoxides can be used. Preferably zirconium acetate is used. The element ratio silicon:heavy metal can therefore be 0.3:1 to 20:1. Preferably the ratio is 2:1 to 8:1.

To produce the torus fillers, either the pure silica sols and/or aqueous mixtures of silica sols and the heavy metal salts were liberated from water and other volatile components. The preferred method to produce spherical, micron-sized non-agglomerated particles is represented by spray drying such sols. To this end, a spray dryer 'Mobile Minor 2000' from Niro A/S, Soborg, Denmark was used. Different geometries of nozzle were tested (two-fluid, centrifugal and fountain nozzles), with incoming air temperatures in the region of 150-300 DEG C, material concentrations in the region of 1-40 wt. %, spray pressure in the region of 2-5 bar and flow rates in the region of 0.2-2.0 Kg/h. Surprisingly, it was found that in the upper region of the different process parameters, particles were formed with a torus shape. FIG. 1 shows SEM pictures of such $SiO_2$ particles which have a torus structure.

Filler particles with an external diameter in the region of 0.5-100 µm, preferably in the region of 1-50 µm can be produced. The diameter of the ring openings lies in the region of 0.2-20 µm, preferably in the region of 0.4-4.0 µm.

Figure 2:
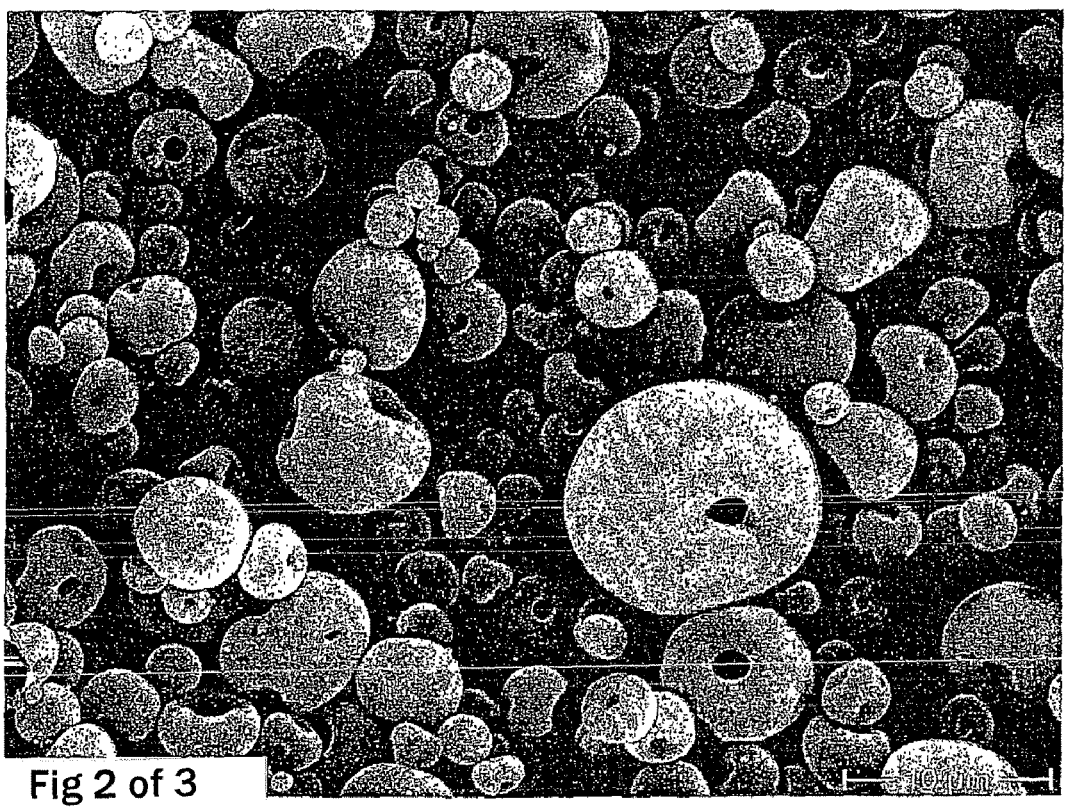
FIG. 2 is a SEM picture showing the torus structure after thermal condensation.
Figure 3:
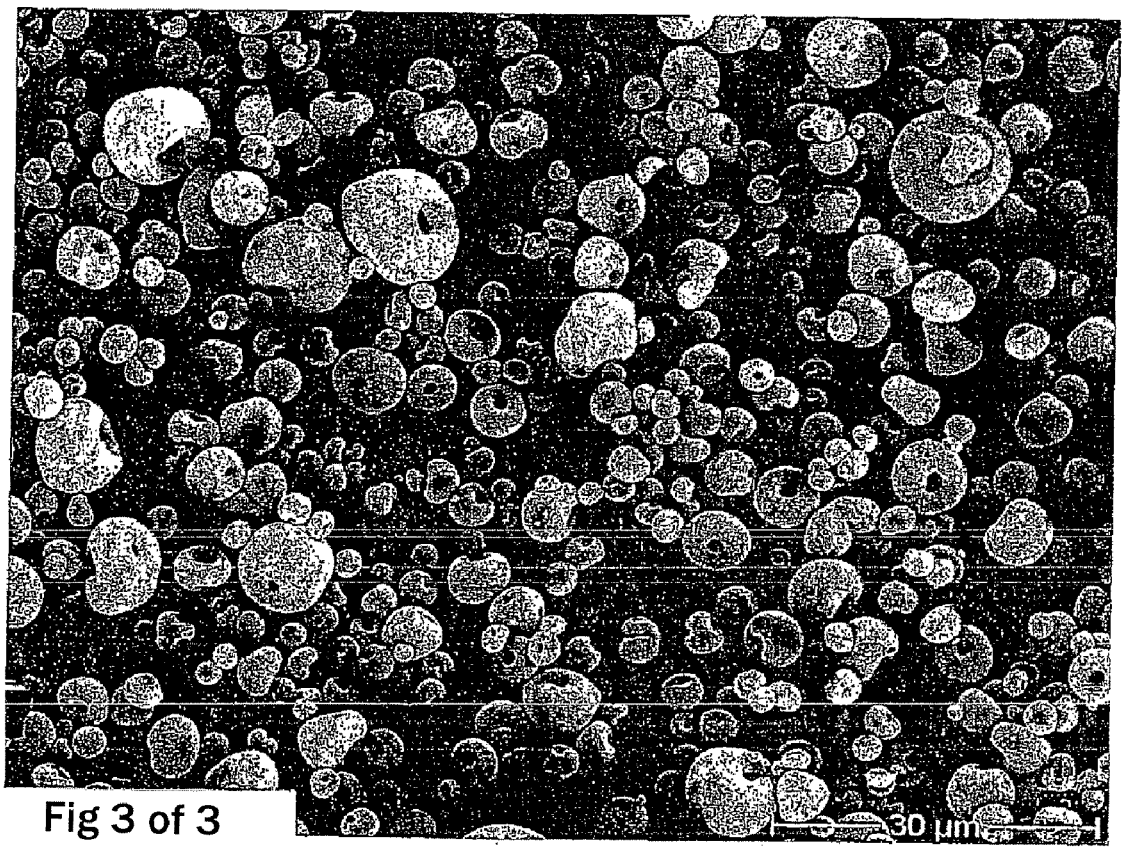
FIG. 3 is a SEM picture after curing at higher temperatures with filler agglomerates.

The particles obtained by spray drying showed moderate mechanical stability and could be destroyed by the effect of shear forces which occur during the production of highly viscous dental filling material. A high mechanical strength of the particles is achieved by calcination. Post-curing of the fillers was carried out at 400-1200 DEG C, preferably at 600-900 DEG C. After post-curing, no reduction in size of the particles is observed. The torus structure also remains unchanged after the thermal condensation (FIG. 2). Post-curing at higher temperatures (800-900 DEG C) leads to filler agglomerates (FIG. 3) which, however, can again be deagglomerated by adding mechanical energy, such as for example ultrasound, and by obtaining the annular structure. The fillers according to the invention are silanized, in order to allow both additional chemical linkage of the fillers to the matrix after curing the composite, and hydrophobing the particle surfaces, which facilitates the flow-through of the filler with the hydrophobic matrix. To this end, 100 g of the filler is added to a solution of 5 g methacryloyloxypropyltrimethoxysilane and 5 g water in 90 g ethanol which is adjusted with acetic acid to a pH value of 5, the solution decanted off after mixing, the filler washed with ethanol, isolated and subsequently dried for 10 minutes at 110 DEG C and 24 hours at room temperature.

EMBODIMENTS

The characteristics of the torus fillers are examined with reference to experimental light curing dental filling composites. To this end, the following composites are formulated in a vacuum planetary mixer and deaerated at low pressure of 0.95 bar.

Triethyleneglycoldimethacrylate (TEDMA), diglycidylmethacrylate of bisphenol-A (BisGMA) and diurethane dimethacrylate (UDMA) were used as ethylenically unsaturated resin components. In example 5 a 40% sol of $SiO_2$ particles with a primary particle size of 15 nm was used in a dimethacrylate mixture Bis-GMA:UDMA:TEDMA of 5:3:2.

In addition to the torus particles according to the invention with an average particle size of 3.0 μm, spherical silicon dioxide particles were used with an average particle size of 3.0 μm, and fragment-like barium-aluminium boron silicate glasses with an average particle size of 3.0 or 0.7 μm. The glass fillers were silanized according to the same process as the torus particles.

Pyrogenic silicic acids (HDK H2000, Wacker, Munich) were used to adjust the consistency to be suitable for processing.

Camphorquinone/4-(N,N-dimethylamino) benzoic acid ethylester (DMABEE) was used as an initiator system for the blue light curing.

The storage stability of the materials was increased by the addition of butylated hydroxytoluene (BHT).

The curing of the sample to carry out material scientific investigations took place with the halogen light apparatus Polofil Lux (VOCO GmbH, Cuxhaven) with a light intensity of 750 mW/cm².

To characterise the strength of the experimental filling composite the flexural breaking strength was determined in accordance with ISO 4049, pt.2.11. The measurement of the polymerisation shrinkage was determined by a dilatometer 30 minutes after exposure. Apparatus construction and methods are disclosed in the publication 'Curing contraction of composites and glass-ionomer cements, A. J. Feilzer, A. J. De Gee, C. L. Davidson, Journal of Prosthetic Dentistry, Vol 59, No. 3, p297-300'. The abrasion resistance of the composite was measured by means of the three-body-wear, disclosed in 'Occlusal wear simulation with the ACTA wear machine, A. J. De Gee, P. Pallav, J. Dent. Suppl. 1 1994, 22, p21-27'.

| Example 1 | |
|---|---|
| Ba-Al-Boron silicate glass, 3.0 μm | 61.2 g |
| Pyrogenic silicic acids | 4.9 g |
| Bis-GMA | 16.9 g |
| UDMA | 10.1 g |
| TEDMA | 6.7 g |
| Camphorquinone | 0.07 g |
| DMABEE | 0.07 g |
| BHT | 0.02 g |

| Example 2 | |
|---|---|
| Spherical $SiO_2$-Particle, 3.0 μm | 61.2 g |
| Pyrogenic silicic acids | 4.9 g |
| Bis-GMA | 16.9 g |
| UDMA | 10.1 g |
| TEDMA | 6.7 g |
| Camphorquinone | 0.07 g |
| DMABEE | 0.07 g |
| BHT | 0.02 g |

| Example 3 | |
|---|---|
| Torus-particle, 3.0 μm | 61.2 g |
| Pyrogenic silicic acid | 4.9 g |
| Bis-GMA | 16.9 g |
| UDMA | 10.1 g |
| TEDMA | 6.7 g |
| Camphorquinone | 0.07 g |
| DMABEE | 0.07 g |
| BHT | 0.02 g |

| Example 4 | |
|---|---|
| Torus-particle, 3.0 mm | 56.2 g |
| Ba-Al-Boron silicate glass, 0.7 mm | 10.0 g |
| Pyrogenic silicic acid | 4.9 g |
| Bis-GMA | 14.9 g |
| UDMA | 8.1 g |
| TEDMA | 5.7 g |
| Camphorquinone | 0.07 g |
| DMABEE | 0.07 g |
| BHT | 0.02 g |

| Example 5 | |
|---|---|
| Torus-particle | 58.5 g |
| 40% $SiO_2$-Sol | 41.3 g |
| Camphorquinone | 0.07 g |
| DMABEE | 0.07 g |
| BHT | 0.02 g |

| | Flexural Strength (MPa) | Abrasion (μm) | Shrinkage (Vol %) |
|---|---|---|---|
| Example 1 | 102 | 3.85 | 77 |
| Example 2 | 104 | 3.41 | 61 |
| Example 3 | 135 | 3.09 | 44 |
| Example 4 | 131 | 2.84 | 39 |
| Example 5 | 144 | 2.49 | 29 |

The exchange of fragment-like glass particles (Example 1) for spherical silicon dioxide particles (Example 2) leads to only a slight improvement of the abrasion resistance and the polymerisation shrinkage.

The comparison with a standard composite composition (Example 1) shows that the replacement of fragment-like glass fillers by the torus fillers according to the invention, with otherwise the same recipe parameters, (Example 3) leads to a greater strength due to the optimal anchoring of the fillers in the cured matrix. This specific anchoring also leads to clearly improved abrasion resistance as the fillers can only be broken out of the piece with difficulty. The high space-filling properties of the inorganic material, due to the spherical structure and favourable packing of the particles bonded thereto, results in lower volume shrinkage.

By the addition of fine glass fillers to the torus particles (Example 4) the inorganic filler component can once again be increased, so that the composite has improved abrasion and shrinkage values.

The use of nanoscale $SiO_2$ particles (Example 5) appears to lead to optimal space filling of the filling materials which once again improves the mechanical properties.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method of filling teeth comprising the steps of:
   1) providing polymerisable composite material as a polymerisable organic binder and a filler, characterised in that it contains filler particles obtained by spray drying sols, post-curing the particles at 800°-1200° C., deagglomerating agglomerates formed, and silanizing the particles thereafter, which particles have the shape of a torus and an average external diameter in the region of 0.5 μm-100 μm and;
   filling cavities in teeth with the material.

2. The method according to claim 1 wherein said composite material additionally contains a silica sol.

3. The method according to claim 1 wherein said composite material is characterised in that, polymerisable organic binder and filler are in a quantity of 1 to 90 wt. %.

4. The method according to claim 2, characterised in that the filler contains 50 to 100 wt. % of the filler particles with the shape of a torus.

5. The method according to claim 1, characterised in that the filler contains additional fragment-shaped and/or spherical inorganic filler particles.

6. The method according to claim 1, characterised in that the filler additionally contains non-torus-shaped filler particles made from silicon dioxide.

7. The method according to claim 6, characterised in that the non-torus-shaped filler particles are produced from pyrogenic and/or precipitated silicic acid and/or silicon dioxide sols and/or from a dispersion of pyrogenic and/or precipitated silicic acid.

8. The method according to claim 1, characterised in that the organic binder includes at least one of the following materials: ethylenically unsaturated monomers and oligomers, epoxides, ormocers, ceramers, liquid crystal systems, spiro-orthoesters, oxethane, polyurethane, polyester, A-silicon and C-silicon, polycarbonic acids.

9. The method according to claim 1, characterised in that the organic binder cures chemically and/or photo chemically.

10. The method according to claim 1, characterised in that the torus-shaped filler particles have an average external diameter in the region of 1 and 50 μm.

11. The method according to claim 1, characterised in that the torus-shaped filler particles have an internal diameter in the region of 0.2-20 μm.

12. The method according to claim 11, characterised in that the torus-shaped filler particles have an internal diameter in the region of 0.4-4.0 μm.

13. The method according to claim 1, characterised in that it contains 15-70 wt. % filler with torus-shaped filler particles.

14. The method according to claim 1, characterised in that the filler particles contain silicon dioxide and/or heavy metal oxides with an atomic number of greater than 28.

15. The method according to claim 14, characterised in that the heavy metal oxides are selected from the group of zirconium oxide, ceroxide, tin oxide, zinc oxide, yttrium oxide, strontium oxide, barium oxide, lanthanum oxide, bismuth oxide and compounds thereof.

* * * * *